(12) United States Patent
Itoh et al.

(10) Patent No.: US 6,899,856 B2
(45) Date of Patent: May 31, 2005

(54) DEVICE FOR GASIFYING STERILIZING LIQUID

(75) Inventors: Yasumasa Itoh, Tokushima (JP); Yasuji Fujikawa, Tokushima (JP); Tadao Akai, Tokushima (JP); Michio Ueda, Tokushima (JP)

(73) Assignee: Shikoku Kakoki Co., Ltd., Itano-Gun (JP)

( * ) Notice: Subject to any disclaimer, the term of this patent is extended or adjusted under 35 U.S.C. 154(b) by 842 days.

(21) Appl. No.: 09/822,230

(22) Filed: Apr. 2, 2001

(65) Prior Publication Data

US 2001/0036430 A1 Nov. 1, 2001

(30) Foreign Application Priority Data

Apr. 4, 2000 (JP) ........................................ 2000-101779

(51) Int. Cl.[7] ................................................. A61L 9/00
(52) U.S. Cl. ........................ 422/305; 422/306; 422/307
(58) Field of Search ................................ 422/305, 306, 422/307, 298, 292

(56) References Cited

U.S. PATENT DOCUMENTS 4,512,935 A * 4/1985 Hilmersson et al. ....... 261/79.2
5,997,827 A * 12/1999 Mezger et al. .............. 422/292

FOREIGN PATENT DOCUMENTS

| EP | 0384 535 A2 | 8/1990 |
| EP | 0 481 361 A1 | 4/1992 |
| JP | 3-226444 | 10/1991 |

* cited by examiner

Primary Examiner—M. Alexandra Elve
(74) Attorney, Agent, or Firm—Armstrong, Kratz, Quintos Hanson & Brooks, LLP.

(57) ABSTRACT

A device for gasifying a sterilizing liquid comprises a hot air duct 12 having an inlet 36 at one end thereof and an outlet 33 at the other end thereof, a hot air generator 37 for supplying to the inlet 36 hot air having a temperature capable of gasifying the sterilizing liquid, a spray nozzle 13 for spraying the sterilizing liquid into the hot air duct 12, and a plate heater 23 disposed as opposed to the outlet 33.

7 Claims, 3 Drawing Sheets

DEVICE FOR GASIFYING STERILIZING LIQUID

BACKGROUND OF THE INVENTION

The present invention relates to gasifying devices, for example, for gasifying the sterilizing liquid to be used for sterilizing container packaging materials.

As disclosed, for example, in JP-A No. 3-226444(1991), devices of the type mentioned are already known which comprise a gasifying tank having a heat generator accommodated therein, a hot air source for supplying to the gasifying tank hot air having a temperature capable of gasifying the sterilizing liquid, and sterilizing liquid supply means for spraying the sterilizing liquid into the gasifying tank or supplying the liquid thereto dropwise.

In the case where the sterilizing liquid is sprayed into contact with the heat generator, a high gasifying efficiency can be achieved, whereas the orifice of the spraying means is likely to be clogged up due to the presence of extraneous matter or precipitation of a stabilizer contained in the sterilizing liquid. Further when a sterilizing agent in the form of fine particles is supplied to the article to be sterilized before being completely gasified, the sterilizing agent is likely to remain on the article. Accordingly there arises a need to additionally provide the step of removing the agent by drying.

If the sterilizing agent is brought into contact with the heat generator dropwise, it is possible to avoid the problems of clogging and permitting the presence of remaining sterilizing agent due to incomplete gasification, whereas evaporation requires a prolonged period of time due to larger particle sizes. Further if the sterilizing agent is placed dropwise into contact with one portion of the heat generator, the heat generator can not be utilized effectively but locally has a portion of lower temperature. Thus, the sterilizing agent fails to evaporate instantaneously, becomes decomposed markedly due to heating and becomes unable to produce a large quantity of gas having a high concentration with good stability. To overcome these problems, that is, to obtain a gas with good stability, the heat generator must be given an increased capacity or the heating surface needs to be utilized effectively.

The conventional device still remains to be improved greatly, for example, in improving the gasifying efficiency, reducing energy consumption, diminishing decomposition of the sterilizing agent, reducing the amount of sterilizing agent to be used, producing a gas of high concentration with high stability and simplifying the device in construction.

SUMMARY OF THE INVENTION

An object of the present invention is to overcome the foregoing problems and provide a device for gasifying a sterilizing liquid efficiently with reduced energy consumption and with the decomposition of the sterilizing agent suppressed, the device permitting use of a reduced amount of the sterilizing agent, affording a gas of high concentration with good stability and having a simple construction to realize these advantages.

The present invention provides a device for gasifying a sterilizing liquid comprising a hot air duct having an inlet at one end thereof and an outlet at the other end thereof, a hot air source for supplying to the inlet hot air having a temperature capable of gasifying the sterilizing liquid, means for spraying the sterilizing liquid into the hot air duct, and a heat generator disposed as opposed to the outlet.

With the sterilizing liquid gasifying device of the present invention, the sterilizing liquid sprayed into the hot air duct is gasified by being mixed with hot air serving as first-stage heating means in a hot atmosphere and is further gasified instantaneously completely by being brought into contact with the heat generator serving as a second-stage heating means. Since a large quantity of gas can be produced, the device is simple in construction. Accordingly, the gasifying device of the invention as used singly is fully serviceable in the case where a plurality of gasifying devices are conventionally needed. Furthermore, the sterilizing liquid can be gasified with suppressed decomposition of the sterilizing agent, while a gas of high concentration can be produced with good stability using a reduced amount of sterilizing agent. This shortens the time needed for sterilization. Moreover, efficient gasification results in diminished energy consumption. The gas obtained has a high temperature and therefore produces a high sterilizing effect.

At least the outlet of the hot air duct and the heat generator are surrounded by a closed gasifying tank, and the gasifying tank has a gas discharge opening on one side of the outlet in the tank opposite to the heat generator on the other side of the outlet. The sterilizing agent discharged from the hot air duct along with hot air is then brought into contact with the heat generator, thereafter turned or reversed and subsequently discharged from the gas discharge opening, so that the path of transport of the sterilizing agent can be longer. This ensures that the sterilizing agent can be heated for a longer period of time and brought into contact with hot air over an increased area, with the result that the agent including large particles can be wholly gasified, while the gas of sterilizing agent can be discharged as held at a high temperature from the gasifying tank.

The hot air duct has a vertical inner duct portion extending through a top wall of the gasifying tank into the tank and having an open lower end providing the outlet, and the gasifying tank has a vertical outer duct portion surrounding the inner duct portion to form a double duct structure along with the inner duct portion and having an open upper end providing the discharge opening, the ratio of the cross sectional area of the inner duct portion to the cross sectional area of a portion between the inner duct portion and the outer duct portion being 1 to 2. This renders the path of transport of the sterilizing agent narrower, making it possible to fully mix the sterilizing agent with the hot air during transport.

When the heat generator is a plate heater disposed on a bottom wall of the gasifying tank so as to be orthogonal to the inner duct portion, fine particles of sterilizing agent which remain liquid without being gasified with the hot air can be effectively converted to a gas.

Further if the hot air has a temperature of at least 300° C., the sterilizing agent can be effectively gasified with the hot air.

The spraying means has a spray nozzle with an orifice positioned within the hot air duct, and the orifice has a diameter of 0.5 mm to 3 mm. The spray nozzle is then free of the likelihood of becoming clogged.

If the spray nozzle is of the two fluid type and when the hot air is supplied at not lower than five times the rate of supply of air to the spray nozzle, it is unlikely that the temperature of the hot air is reduced by the air for spraying the sterilizing agent, as substantially influenced by the air for spraying.

DESCRIPTION OF THE PREFERRED EMBODIMENTS

Embodiments of the present invention will be described next with reference to the drawings.

Figure 1:
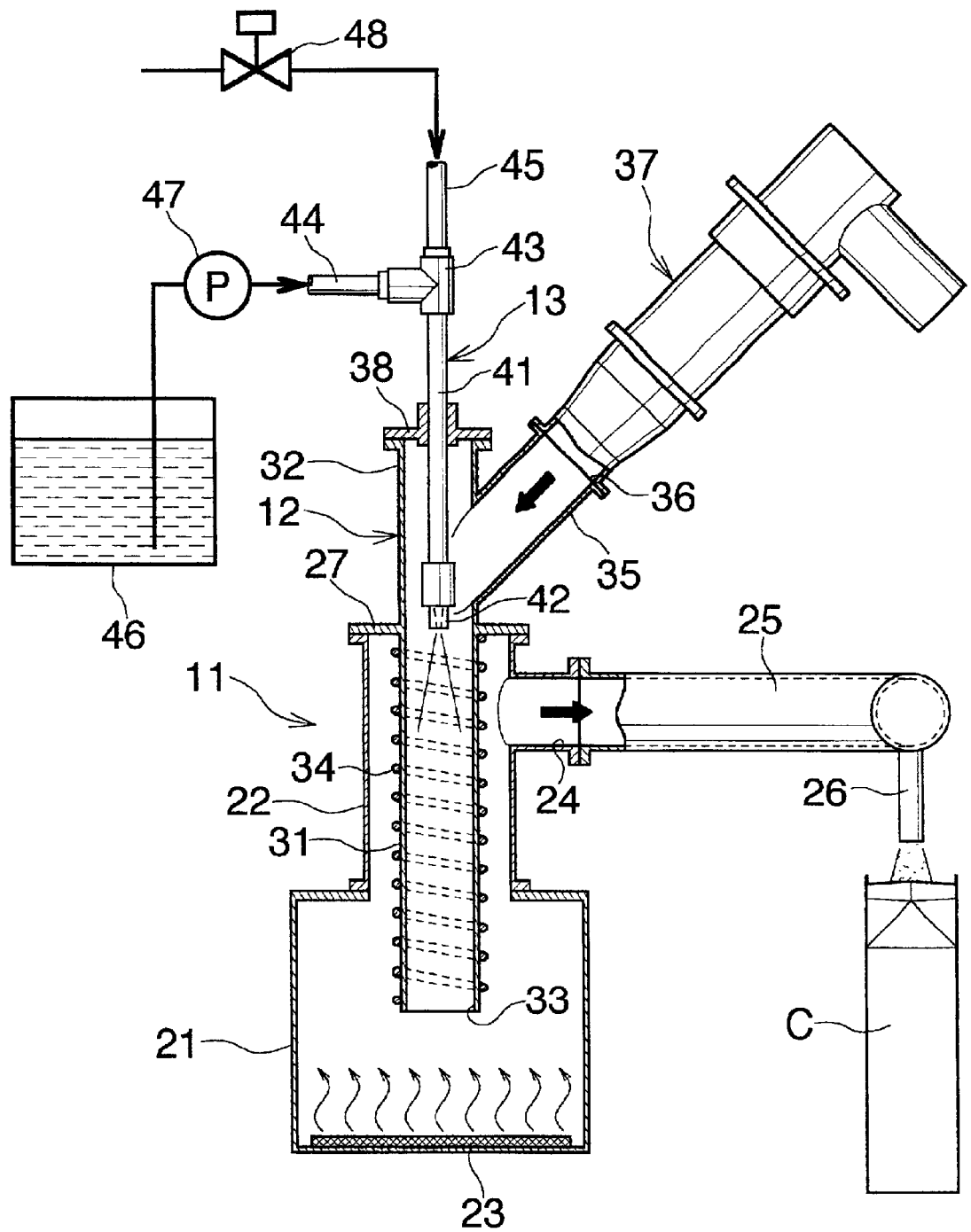
FIG. 1 is a view in vertical longitudinal section of a gasifying device of the invention.

FIG. 1 shows a sterilizing liquid gasifying device, which comprises a gasifying tank 11, a hot air duct 12 for supplying hot air to the tank 11, and a spray nozzle 13 for spraying a sterilizing agent into the hot air duct 12.

The gasifying tank 11 comprises a lower tank 21 having a large diameter and in the form of a vertical short tube, and an upper tank 22 of small diameter in the form of a vertical tube and extending upright from the top wall of the tank 21. A plate heater 23 is provided on the bottom wall of the lower tank 21. The upper tank 22 has an outlet 24 formed in an upper end portion of the peripheral wall thereof. Connected to the outlet 24 is the inlet end of a guide duct 25. The guide duct 25 has an outlet end connected to a gas nozzle 26 disposed above a container C. A lower top plate 27 is provided on the upper end of the upper tank 22.

The hot air duct 12 comprises a lower vertical portion 31 extending through the lower top wall 27 into the upper tank 22, and an upper vertical portion 32 projecting outward from the upper tank 22. The lower vertical portion 31 is disposed concentrically with the upper tank 22, providing a double tube structure along with the upper tank 22. The ratio of the cross sectional area of the lower vertical portion 31 to the cross sectional area of the portion between the lower vertical portion 31 and the upper tank 22 is approximately 1:1.5.

The lower vertical portion 31 has a lower part projecting downward from the upper tank 22 into the lower tank 21. The lower end of the lower vertical portion 31 is positioned in the vicinity of the plate heater 23 and opened to provide an outlet 33. A wire heater 34 is helically wound around the lower vertical portion 31. The wire heater 34 has a temperature of 300° C.

The upper vertical portion 32 is provided with a slanting tubular connector 35 having an open upper end providing an inlet 36. Connected to the inlet end 36 is an air outlet of a hot air generator 37. An upper top plate 38 is provided on the upper end of the upper vertical portion 32.

The spray nozzle 13 comprises a nozzle body 41 in the form of a vertical tube and extending through the upper top plate 38, and an orifice member 42 fitted in a lower-end opening of the nozzle body 41.

A sterilizing liquid supply pipe 44 and an air supply pipe 45 are connected at their outlet ends to an open upper end of the nozzle body 41 by a coupling member 43. The other end of the sterilizing liquid supply pipe 44 is connected to a sterilizing liquid tank 46. The other end of the air supply pipe 45 is connected to an unillustrated pressurized air source. The liquid supply pipe 44 is provided with a metering pump 47, and the air supply pipe 45 with a regulator 48.

Figure 2:
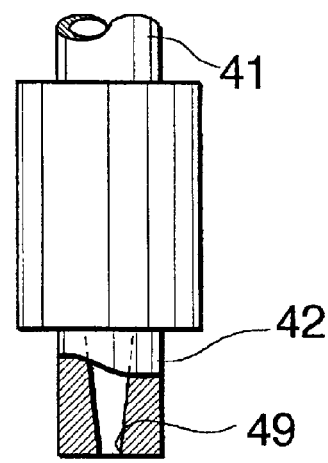
FIG. 2 is a side elevation showing a spray nozzle 13 of the gasifying device in detail.

As shown in detail in FIG. 2, a downwardly tapered orifice 49 is formed in the orifice member 42 in alignment with its axis. The orifice 49 has a lower-end opening diameter of 0.5 mm to 3 mm, most suitably 1 mm to 2 mm. This orifice size is considerably greater than the orifices of known two-fluid nozzles (not shown) for producing fine particles by collision.

When hot air is sent into the hot air duct 12 from the hot air generator 37, with mist of sterilizing liquid forced into the duct 12 from the spray nozzle 13 at the same time, the mist is gasified with the hot air in a first stage while passing through the hot air duct 12. When the hot air duct 12 is heated by the wire heater 34 in this case, the sterilizing liquid can be gasified effectively.

On gasification, the sterilizing liquid flows out of the hot air duct 12, coming into striking contact with the plate heater 23, whereby the liquid is gasified in a second stage. The sterilizing liquid thus gasified almost completely is turned upward by striking contact with the plate heater 23 and discharged from the gasifying tank 11 through the outlet 24. In the meantime, the gasification of the sterilizing liquid proceeds continuously. If heated by the wire heater 34, the hot air duct 12 can be held at a high temperature at all times. This is effective for completely gasifying the whole sterilizing agent including large particles and allowing the gas of sterilizing agent to flow out of the tank 11 while retaining a high temperature. The gas of sterilizing liquid discharged from the outlet 24 is led to the position of the container C by the guide duct 25 and sprayed into the container C by the nozzle 26.

Figure 3:
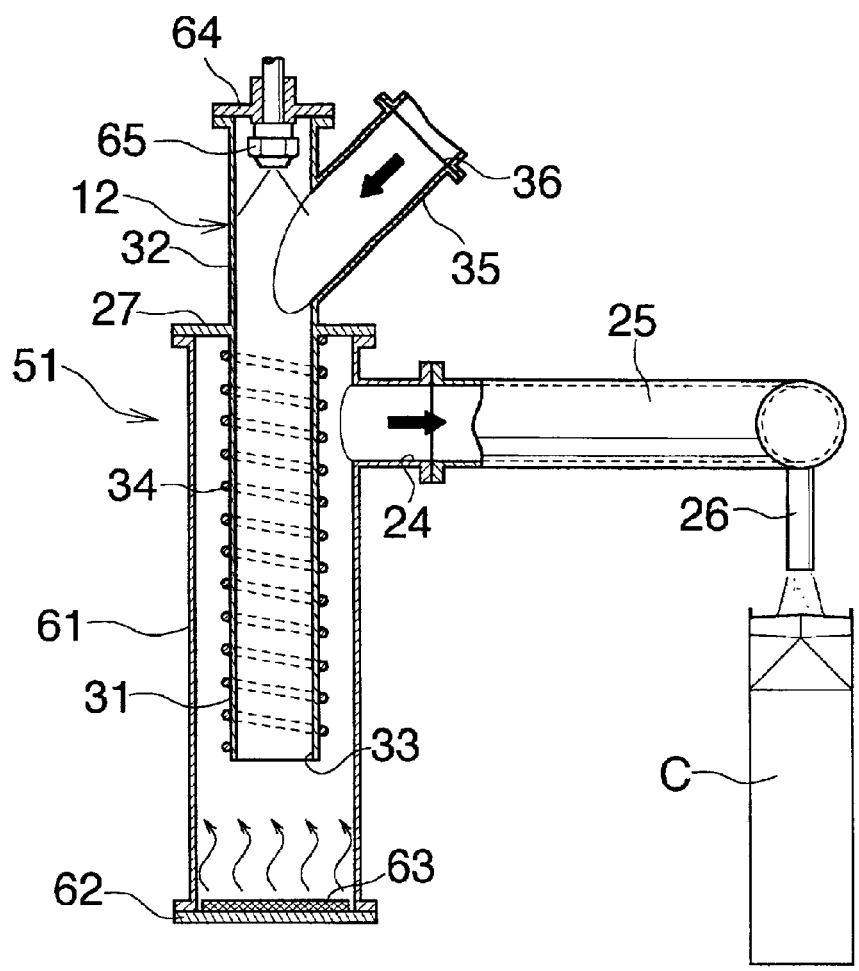
FIG. 3 is a view in section corresponding to FIG. 1 and showing a modification of the gasifying device.

FIG. 3 shows a modified gasifying device. In FIGS. 1 and 3, like parts are designated by like reference numerals and will not be described repeatedly. The difference only will be described below.

The modified gasifying device comprises a gasifying tank 51, which comprises a tank body 61 in the form of a vertical tube and having a uniform cross section over the entire length thereof. The tank body 61 is provided at its lower end with a bottom plate 62, with a plate heater 63 placed on its upper surface. A spray nozzle 65 is mounted on a top plate 64 of a hot air duct 12. The spray nozzle 65 is not of the two-fluid type but of the single fluid type having a conical spray pattern.

The device of the present invention was checked for performance by various tests. For comparison, the conventional device described first with reference to the prior art was similarly tested for spraying a sterilizing agent.

Test 1: Vaporization Capacity

An aqueous solution (35%) of hydrogen peroxide was gasified while being supplied at a gradually increasing rate to determine as a vaporization capacity (maximum rate of evaporation) the rate of supply of the solution at which the solution evaporating instantaneously on the plate heater 23 started to partly remain thereon as a liquid without gasification. The test conditions are as follows.

| | |
|---|---|
| Air pressue for spraying the solution: | 0.2 MPa |
| Hot air generator: | 3 kW |
| Rate of supply of hot air: | 0.3 m³/min |
| Temperature of hot air: | 300° C. |
| Temperature of plate heater: | 300° C. (3 kW) |

TABLE 1

Vaporization Capacity

| | Vaporization capacity |
|---|---|
| Invention device | 80 ml/min |
| Conventional device | 60 ml/min |

Table 1 reveals that the solution can be gasified at a higher rate by the device of the invention than by the conventional device.

Test 2: Effect of Plate Heater

The device of the invention only was tested to determine the influence of the presence or absence of the plate heater 23 on the vaporization capacity. To determine the vaporization capacity in the absence of the plate heater 23, the rate of supply of an aqueous solution of hydrogen peroxide was measured at which the solution started to adhere as liquid drops on the inner surface of the hot air duct 12 without evaporation. Table 2 shows the result. Table 2 reveals that the use of the plate heater 23 exerts a very great influence.

TABLE 2

Effect of Plate Heater

| Plate heater | Vaporization capacity | Total energy |
|---|---|---|
| Used | 80 ml/min | 6 kW |
| Not used | 25 ml/min | 3 kW |

Test 3: Decomposition Ratio of Hydrogen Peroxide

The device of the invention and the conventional device were tested for gasification under the same conditions as in Test 1, with the solution of hydrogen peroxide supplied at the rate to effect the maximum rate of evaporation and also at a rate to result in an evaporation rate of 80% of the maximum. The gas obtained by each device was condensed by a cooling device and then collected to obtain a sample, which was checked for concentration. The result is shown in Table 3, which reveals that the hydrogen peroxide produced by the device of the invention exhibited a suppressed decomposition ratio and had a high concentration, hence efficient gasification.

TABLE 3

Hydrogen Peroxide Decomposition Ratio

| | Evaporation rate | Decomp. ratio |
|---|---|---|
| Invention device | 80 ml/min | 30% |
| | 64 ml/min | 10% |
| Conventional device | 60 ml/min | 50% |
| | 48 ml/min | 30% |

Test 4: Gas Temperature

The device of the invention and the conventional device were tested for gasification under the same conditions as in Test 1, with the solution of hydrogen peroxide supplied at a rate to result in an evaporation rate of 80% of the maximum rate of evaporation, and the temperature of the gas discharged was measured. Table 4 shows that the device of the invention produced a gas of higher temperature than the conventional device.

TABLE 4

Gas Temperature

| | Evaporation rate | Gas temp. |
|---|---|---|
| Invention device | 64 ml/min | 170° C. |
| Conventional device | 48 ml/min | 130° C. |

Test 5: Sterilizing Effect

Spores of *B. subtilis* were applied to the inner surfaces of 1000-ml cartons. The device of the invention and the conventional device were each used for gasification under the same conditions as in Test 1 by supplying 35% aqueous solutions of hydrogen peroxide at a rate of 30 ml/min, and the gas obtained was sprayed onto cartons for 1 second and then dried for 3 seconds for removal. Using the sterilized cartons as samples and untreated cartons as blanks, the effect of sterilization was determined from the following equation. Table 5 shows the result.

$$\text{Sterilizing effect} = \log(A/B)$$

wherein A is the average number of spores on the blank, and B is the average number of surviving spores on the sample.

TABLE 5

Sterilizing Effect

| | Sterilizing effect |
|---|---|
| Invention device | 4.0 |
| Conventional device | 2.0 |

The conventional device is 2.0 in sterilizing effect, whereas the device of the invention is 4.0 in sterilizing effect. Since the device of the invention gasifies the sterilizing agent efficiently, the gas obtained is higher in concentration and temperature to exhibit a higher sterilizing effect than the gas produced by the conventional device using the same amount of sterilizing agent.

The foregoing test results indicate that the device of the invention is adapted for efficient gasification, therefore produces a larger amount of gas than the conventional device, is diminished in energy consumption and assures suppressed decomposition of the sterilizing agent to reduce the amount of the sterilizing agent to be used. It will be understood that since the present device has a double tube structure, the gas can be guided to containers while retaining a high temperature without becoming mixed with particles of the sterilizing agent remaining to be gasified completely to exhibit a high sterilizing effect.

Figure 4:
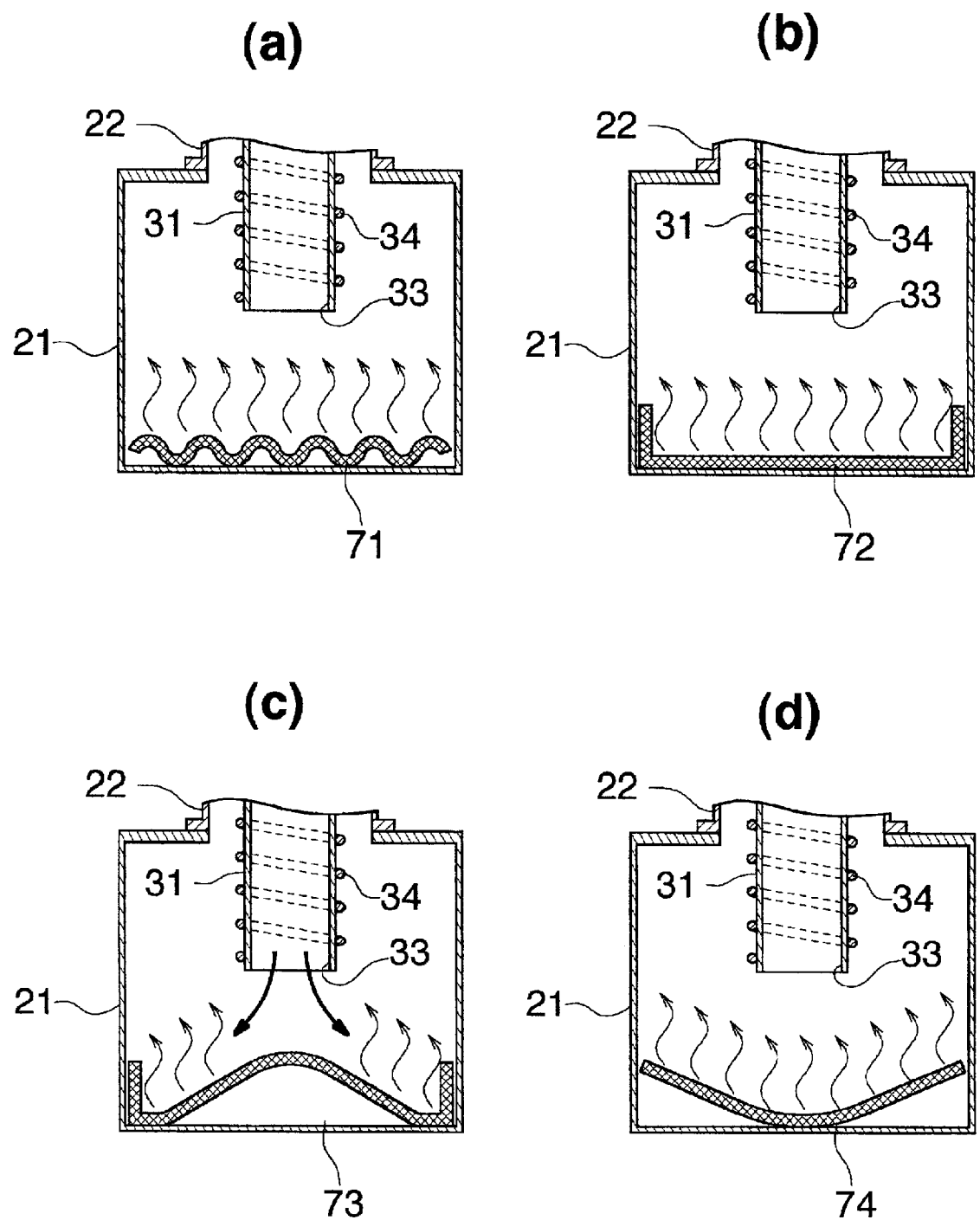
FIG. 4 includes views in section showing modified plate heaters.

FIG. 4 shows modified plate heaters. FIG. 4(a) shows a plate heater 71 which is made wavy in cross section and thereby given an increased surface area. FIG. 4(b) shows a dishlike plate heater 72 which is similarly given an increased surface area. FIG. 4(c) shows a plate heater 73 having a raised central portion for permitting hot air to flow toward outer peripheral portion easily upon turning or reversing. FIG. 4(d) shows a plate heater 74 having a recessed central portion for permitting hot air to flow upward readily upon turning.

What is claimed is:

1. A device for gasifying a sterilizing liquid comprising a hot air duct having an inlet at one end thereof and an outlet at the other end thereof, a hot air source for supplying to the inlet hot air having a temperature capable of gasifying the sterilizing liquid, means for spraying the sterilizing liquid into the hot air duct, and a heat generator disposed opposite to the outlet, wherein at least the outlet of the hot air duct and the heat generator are surrounded by a closed gasifying tank, and the gasifying tank has a gas discharge opening on one side of the outlet in the tank opposite to the heat generator on the other side of the outlet.

2. A device for gasifying a sterilizing liquid comprising a hot air duct having an inlet at one end thereof and an outlet at the other end thereof, a hot air source for supplying to the inlet hot air having a temperature capable of gasifying the sterilizing liquid, means for spraying the sterilizing liquid into the hot air duct, and a heat generator disposed opposite to the outlet, wherein the hot air duct includes an inner duct portion extending through a wall of the tank and having an open end providing the outlet, the tank has an outer duct portion surrounding at least a portion of the inner duct portion and being spaced apart from the inner duct portion to form a double duct structure, the inner and outer duct portions are disposed concentrically, the hot air source supplies the hot air directly to the inner duct portion through the inlet, and the outer duct portion provides a gas discharge opening.

3. A device for gasifying a sterilizing liquid comprising a hot air duct having an inlet at one end thereof and an outlet at the other end thereof, a hot air source for supplying to the inlet hot air having a temperature capable of gasifying the sterilizing liquid, means for spraying the sterilizing liquid into the hot air duct, and a heat generator disposed opposite to the outlet, wherein at least the outlet of the hot air duct and the heat generator are surrounded by a closed gasifying tank, and the gasifying tank has a gas discharge opening on one side of the outlet in the tank opposite to the heat generator on the other side of the outlet, and wherein the hot air duct has a vertical inner duct portion extending through a top wall of the gasifying tank into the tank and having an open lower end providing the outlet, and the gasifying tank has a vertical outer duct portion surrounding the inner duct portion to form a double duct structure along with the inner duct portion and having an open upper end providing the discharge opening, the ratio of the cross sectional area of the inner duct portion to the cross sectional area of a portion between the inner duct portion and the outer duct portion being 1 to 2.

4. A sterilizing liquid gasifying device according to claim 3 wherein the heat generator is a plate heater disposed on a bottom wall of the gasifying tank so as to be orthogonal to the inner duct portion.

5. A sterilizing liquid gasifying device according to any one of claims 1 to 4 wherein the hot air has a temperature of at least 300 C.

6. A sterilizing liquid gasifying device according to any one of claims 1 to 4 wherein the spraying means has a spray nozzle with an orifice positioned within the hot air duct, and the orifice has a diameter of 0.5 mm to 3 mm.

7. A sterilizing liquid gasifying device according to claim 6 wherein the spray nozzle is of the two fluid type, and the hot air is supplied at not lower than five times the rate of supply of air to the spray nozzle.

* * * * *